US006572841B1

(12) United States Patent
Mautone

(10) Patent No.: US 6,572,841 B1
(45) Date of Patent: Jun. 3, 2003

(54) COMPOSITION AND METHOD FOR DECREASING UPPER RESPIRATORY AIRWAY RESISTANCE

(75) Inventor: Alan J. Mautone, Morristown, NJ (US)

(73) Assignee: Scientific Development and Research, Inc, Belleville, NJ (US)

( * ) Notice: Subject to any disclaimer, the term of this patent is extended or adjusted under 35 U.S.C. 154(b) by 0 days.

(21) Appl. No.: 09/639,739

(22) Filed: Aug. 16, 2000

Related U.S. Application Data

(63) Continuation-in-part of application No. 09/450,884, filed on Nov. 28, 1999.

(51) Int. Cl.[7] .............................. A61L 9/02; A61K 9/72; A61K 9/12

(52) U.S. Cl. .............................. 424/45; 424/40; 424/47; 424/450

(58) Field of Search .............................. 424/45, 40, 47, 424/450

(56) References Cited

U.S. PATENT DOCUMENTS

| | | | | | |
|---|---|---|---|---|---|
| 4,765,987 | A | | 8/1988 | Bonte | |
| 5,053,217 | A | | 10/1991 | Lehigh | |
| 5,141,674 | A | * | 8/1992 | Leigh | 252/305 |
| 5,192,528 | A | | 3/1993 | Ramachandran | |
| 5,306,483 | A | * | 4/1994 | Mautone | 424/45 |
| 5,958,378 | A | | 9/1999 | Waldrep | |
| 6,045,828 | A | | 4/2000 | Bystrom | |
| 6,063,400 | A | | 5/2000 | Geho | |
| 6,156,294 | A | * | 12/2000 | Mautone | 424/45 |

* cited by examiner

*Primary Examiner*—Frederick Krass
*Assistant Examiner*—Donna Jagoe
(74) *Attorney, Agent, or Firm*—Richard L. Strauss, Esq.

(57) ABSTRACT

The present invention discloses a method of decreasing airflow resistance through the mammalian upper respiratory system by administering an aerosolized mixture of lipid crystals comprised of a mixture of one or more lipids surfactants and one or more spreading agents selected from the group consisting of cholesteryl esters, phospholipids, carbohydrates and proteins, in powder form, and one or more fluorocarbon propellants, through nasal or oral inhalation. Upon administration, the propellant(s) are evaporated from the mixture and the lipid crystals are deposited upon the air/liquid interface resident upon epithelial tissue lining air ways and air spaces of said upper respiratory system. Upon contact of said lipid crystals with the air/liquid interface, an amorphous spread film is formed thereupon substantially decreasing the surface tension of said lining and resulting in an increase in volume of said airways and airspaces. In a second preferred embodiment, a therapeutically active agent effective in the treatment of upper respiratory disease is added to the mixture of lipid crystals and upon administration of said aerosol mixture, the amorphous spread film formed thereby carries said therapeutically active agent throughout the epithelium of said upper respiratory system so as to improve airflow through the upper respiratory system by both reducing surface tension of the epithelial lining and by effectively treating the inflammatory process.

53 Claims, No Drawings

COMPOSITION AND METHOD FOR DECREASING UPPER RESPIRATORY AIRWAY RESISTANCE

This is a continuation-in-part of U.S. patent application Ser. No. 09/450,884 filed on Nov. 28, 1999, the entire specification of which is hereby incorporated by reference.

FIELD OF INVENTION

The present invention relates to the field of pharmacological compositions and methods of utilizing such compositions in order to improve air flow throughout the upper respiratory system. More specifically, the present invention discloses compositions having powerful surfactant effect upon the air/liquid interface resident upon the epithelial lining of the upper respiratory system—and the use of such compounds—in order to open air spaces and air ways which have become partially or completely obstructed by proximal epithelial wall collapse and/or adhesion caused by the presence and effect of highly viscous mucous exudate—generated as a product of inflammatory response—secreted thereupon.

BACKGROUND OF THE INVENTION

Pathological conditions can arise from, and can cause changes in surface tension values of air/liquid interfaces resident upon tissue surfaces, especially epithelial surface tissues, of and within various organs of mammalian anatomy. The naturally occurring "surfactant system" secreted upon the epithelial lining of the lung which is deficient in cases of R.D.S. is known to be comprised of a complex mixture of lipids, proteins and carbohydrates (as described in a recent review: Surfactants and the Lining of the Lung, The John Hopkinds University Press, Baltimore, 1988).

The prime function of the surfactant system is to stabilize the alveoli and associated small airways against collapse by decreasing the surface tension at the air/liquid interface. It is now believed that the action of the phospholipid component of the surfactant system is the principal source of the powerful surface tension reduction effect of the naturally occurring surfactant system of the lung. More specifically, it is known that the fully saturated diacylphospholipids, principally dipalmitoyl phosphatidylcholine (DPPC), provide liquid balance and anti-collapse properties to the lung's epithelial lining. In addition to DPPC, spreading agents, also found within the naturally occurring surfactant system, assist DPPC in rapidly forming a uniform spread film on the air/liquid surfaces of the lung. Such spreading agents include cholesteryl esters such as, for example, cholesteryl palmitate (CP); phospholipids such as, for example, diacylophosphatidylglycerols (PG), diacylphosphatidylethanolamines (PE), diacylphosphatidylserines (PS), diacylphosphatidylinositols (PI), sphingomelin (Sph) and Cardiolipin (Card) and virtually and other phospholipid, and the lysophospholipids; or any of the plasmalogens, dialklylphospholipids, phosphonolipids; carbohydrates and proteins, such as, for example, albumin, pulmonary surfactant proteins A, B, C and D. The naturally occurring surfactant system is further described in U.S. Pat. No. 5,306,483.

DPPC has been administered to infants with respiratory distress syndrome as a therapeutic measure in order to restore deficient or low levels of natural surfactant. For this purpose, DPPC has been administered by means of an aqueous aerosol generator (utilized with an incubator in which the infant resided during treatment). Endotracheal administration has also been utilized. DPPC therapy has been typified as utilizing natural surfactants (harvested from porcine or bovine lungs), or artificial, commercially synthesized compounds.

It has also heretofore been disclosed to utilize therapeutic agents, in combination with surfactant/spreading agents to effectively administer drug therapy uniformly throughout the epithelial lining of the lung. U.S. Pat. No. 5,306,483 (the "'483 patent") discloses a process to prepare lipid crystalline figures in fluorocarbon propellants for the delivery of therapeutically active substances which form amorphous fluids on delivery at the air/liquid interface of the lung and which can be utilized as an effective drug delivery system. More specifically, said patent discloses a process comprising (a) preparing a mixture of one or more lipids of the group of phospholipids known as phosphatidylcholines and one or more spreading agents, in powder form and a therapeutically active substance and one or more fluorocarbon propellants, said lipids, spreading agents and therapeutically active substances being insoluble in the propellants; and (b) evaporating the propellants from the mixture. The '483 patent teaches the combination of dipalmitoyl phosphatidylcholine (DPPC) or any of the other fully saturated Acyl chain phospholipids, 80.0 to 99.5% by weight, and other spreading agents, for example, phospholipids such as, but not limited to PG, PE, PS, PI, lysophospholipids, plasmalogens, dialkylphospholipids, diether phosphonolipids, Cardiolipin, sphingomyelin, 0.5 to 20.0% weight; neutral lipids like cholesteryl esters such as, but no limited to, cholesteryl palmitate, cholesteryl oleate, cholesteryl stearate, 0.5 to 10% by weight, carbohydrates, such as, but not limited to, glucose, fructose, galactose, pneumogalactan, dextrose, 0.5 to 10% by weight; and proteins such as, but not limited to albumin, pulmonary surfactant specific proteins A, B, C, and D 0.5 to 10% by weight, yielding lipid-crystalline structures in fluorocarbon (both chloro- and hydrofluorocarbon) propellants in which therapeutically active agents, drugs and other materials can be carried into the lungs after release from and through metered dose nebulizer. The spreading agents referred to in the '483 patent are compounds such as the above-described phospholipids, lysophospholipids, plasmalogens, dialklyphospholipids, phosphonolipids, carbohydrates and proteins. The function of the spreading agent is to assist DPPC, or other phospholipids such as, for example, DPPG, in rapidly adsorbing and forming a spread film upon the air/liquid surfaces of the lungs. In addition, the '483 patent also discloses a process for preparing such lipid crystalline figures in fluorocarbon propellants without a therapeutically active substance for use as a tear (as for the eye).

The mammalian upper respiratory system is comprised of various conduits and chambers especially adapted for conduction of air to and away from the lungs. Besides forming a simple conduit, the upper respiratory system is responsible for warming, moisturizing, and removal, by means of entrapment and filtration, the various impurities found in inspired air so as to protect the lower respiratory system from disease and irritation, while simultaneously conditioning inspired air for maximum gas exchange. Generally, the upper respiratory system can be said to be comprised of the nose, nasal cavity, nasopharynx, paranasal sinuses, oropharynx and laryngopharynx.

As ambient air is inspired through the nose, it first passes through the external nares where relatively large hairs filter and remove larger particles from the air stream. From the external nares, the air is then drawn through the nasal cavity for further filtration. Within the nasal cavity, small boney protuberances known as the nasal conchae line the lateral walls of the chamber. The conchae, also known as turbinate bones, create great turbulence within the inspired air. The conchae thereby increase the collision and contact of smaller particulate matter with the adherent mucous coating of the epithelial surfaces lining the nasal cavity. Thus, such particles that avoid filtration by nasal hairs may become trapped within the nasal cavity. Mucous producing goblet cells which create the mucous coating of the upper respiratory system, assisted by the movement of cilia located on the free border of the epithelial cells, acts to continually flush such particulate matter, and any organisms which they may carry, towards the pharynx where they are swallowed and any such organisms destroyed in the acidic environment of the stomach. In addition, mucous production may also flush such matter out of the system through the external nares.

The paranasal sinuses also act as a filtration system in that the mucous membranes lining the sinuses also tend to trap impurities entering these structures during inspiration. Likewise, the nasopharynx, lined with respiratory epithelium, is also covered with mucoid secretions and capable of trapping and eliminating particulate contaminants in a similar manner.

As stated above, the upper respiratory system provides a conduit for the passage of air to the lungs. During normal physiologic function, the filtering structures and activities of the upper respiratory system do not interfere or present increased resistance to inspiration. However, during times of increased inflammatory activity, localized edema, or swelling of nasal and sinus membranes, can cause great resistance to normal respiration.

As discussed in greater detail below, inspired antigenic material can induce, through the inflammatory response, a marked increase in goblet cell mucous production. In addition, the inflammatory response quite often results in increased permeability of capillaries located close to the epithelial lining. Such increased permeability results in a localized edema or swelling of the epithelial lining of the upper respiratory system as various components of blood seep into the interstitial spaces. More specifically, such increased permeability allows the entry of white cells into the epithelial tissue where they may complex with the antigenic trigger of the inflammatory reaction resulting in phagocytosis, lysis, and enzymatic destruction of such foreign material. The localized edema—observed as substantial swelling of the epithelial lining of the upper respiratory system—tends to narrow the airways and airspaces. In addition, another common inflammatory response to antigenic challenge is the increased production of mucous and secretion of same upon the epithelial lining. The proteinaceous remnants of inflammatory phagocytosis, lysis and enzymatic destruction, discussed above, combines with the increased quantity of mucous to form an unusually viscous mucous coating upon the epithelial lining exhibiting higher levels of surface tension.

During the course of upper respiratory inflammation—characterized by the aforementioned edema and copious viscous mucous—opposing mucous laden epithelial surfaces lining the nasal cavity and sinuses—that ordinarily provide the above-described filtering functions—may become so swollen as to contact one another and so reduce airway volume. In addition, such swelling may be great enough, in the case of sections of the airway and airspaces demonstrating diminutive diameter, to allow proximal and/or opposing epithelial surfaces to come into direct continuous or intermittent contact. Upon such contact, the viscous mucoid exudate resident upon such surfaces may cause, due to the high surface tension properties discussed above, partial or complete closure of such air ways and air spaces.

For example, during the course of a common cold, bout of influenza, bacterial infection or allergy attack, antigenic proteins of such viruses, bacteria, and/or antigenic particles (for example, pollens, dust, dust mites, or other particulate antigenic material) present in inspired air may become trapped upon the normally present mucous coating of the lining epithelium whereupon the come into contact with macrophages. Such macrophages may induce an initial immune response by presenting such antigenic material to T-lymphocytes such as, for example, a CD4+ T lymphocyte. Upon such presentation, CD4+ lymphocytes respond, in part, by releasing a multitude of interleukins and cytokines which, in turn, promote the production of IgE. Mast cells, in close proximity with capillaries of the upper respiratory mucosa are induced by action of such IgE to secrete histamine. At the same time, histamine production increases both the volume of blood entering the tissue from local capillaries as well as increasing goblet cell production of mucous. In addition, presentation of antigen to lymphocyte leads to a cascade of inflammatory activity wherein pmns, with activated antibody, leach out of capillaries which have been made permeable thereto by histamine, into the respiratory epithelium wherein they complex with antigen for phagcytotic, lytic and macrophagic activities. The release of arachidonic acid from such activated mast cells, macrophages and pmns may lead to, for example, the production of luekotrienes. Luekotrienes, have inflammatory effects similar to histamine. However, luekotrienes effect such chemotaxis and enhanced mucous production to a far greater degree than histamine.

As discussed above, histamine and luekotrienes both act to vastly increase capillary permeability which, in turn, results in a general swelling of the mucosa as additional anti-body laden white blood cells leach out of said capillaries to form antibody-antigen complexes. Phagocytosis of such complexes by pmns, macrophages, and/or annihilation by means of the complement destruction cascade produces much waste material. This highly proteinaceous material, when added to the increased mucous secretions induced by these inflammatory pathways, forms copious amounts of viscous mucous resident upon said epithelial lining exhibiting substantially greater surface tension than that generated by the air/liquid interface of the epithelial lining in the absence of inflammation.

Two inflammatory effects, localized edema and increased exudate surface tension act, in concert, to promote and enable the above-described attraction and adhesion of proximal epithelial surfaces to one another leading to increased air way and air space resistance. However, it is the high surface tension properties of the mucoid secretions that allow and promote proximal inflamed tissues to remain adherent upon each other. In the absence of such increased surface tension, edema alone would, in many instances, only result in intermittent contact of proximal surfaces of the epithelial lining.

It has been heretofore possible to treat the underlying immune response with drugs effective in decreasing or eliminating same. For example, reduction of the production of mucous secretions is well known through the use of both anti-histamines and antiluekotreines. Indeed, such drug therapy may be effective in opening portions of the upper respiratory system closed by the combination of edema and increased mucous production discussed above. However, the use of anti-histamines may have undesired side effects such as, for example, drowsiness as they are often systemic in effect. Certain medications effective at reducing mucous production and inflammation such as, for example, pseudoephedrine, may cause nervousness, dry mouth, and other effects. Generally, undesirable side effects of such antihistamine type medications are dose dependent with greater dosage—required in some instances to effectively reduce viscous mucous production, and decrease edema—leading to an increase in such side and adverse effects. In addition, although mucous production may be annoying and uncomfortable, increased production of mucous and increased activity of the muco-ciliary transport system during the course of an upper respiratory infection serves the important function of flushing out bacteria while simultaneously preventing infection spread to the lung. Therefore, a drastic decrease or elimination of mucous production during the course of upper respiratory inflammatory episodes is not necessarily a desirable mode of treatment.

What is needed is a composition and method of delivering same which is effective in lowering the surface tension of the increased viscous mucous produced during inflammation of the upper respiratory system without effecting the purging effect of the muco-ciliary system, but rather assisting said system in washing out by products of the inflammatory process from the upper respiratory system while promoting the opening of the air spaces and air ways within.

Although the above-described medications may have undesirable side effects, such effects, systemic in nature, may be reduced by application of reduced amounts of such agents directly to the effected the upper respiratory epithelium. Thus, such therapeutics, administered via nasal inhalation, may be utilized to place the maximum amount of agent on the target tissue while minimizing systemic exposure. However, it has heretofore not been possible to ensure that such medication, delivered via nasal inhalation, was delivered uniformly upon the epithelial surfaces of the upper respiratory system. What has been needed is a therapeutic agent carrier capable of providing direct and uniform application of such agents directly to such target tissue.

It is known that an analogous increase in surface tension occurs during episodes of otitis media. Otitis media is a pathological condition common to mammalian species, and most common to children. During episodes of otitis media, fluid accumulates in the middle ear or, as it is also known, the tympanic cavity.

Although, as described below, surfactant compositions, both natural and artificial, have been heretofore known, formulated and utilized to decrease surface tension within the lung, no such compositions, or methods for administering said compositions, have been heretofore suggested, taught or disclosed in regards to decreasing the surface tension within the lumen of the eustachian tube. Likewise, no method has heretofore been known which provides an effective decrease in opening resistance of the eustachian tube while simultaneously enhancing the pressure equilibration functions thereof.

Additionally, although such surfactant compositions have been known, formulated and utilized to decrease surface tension within the lungs, no such compositions, or methods of administering said compositions, have been heretofore suggested, taught or disclosed in regards to decreasing the surface tension of the epithelial mucosa lining the upper respiratory system so as to decrease the resistance to air flow therethrough or to utilize such methods and compositions to provide an improved and highly effective means of delivering therapeutic agents effective in the treatment of upper respiratory disorders, such as for example, bacterial infections, viral infections and allergies which may all result in the above-described swelling, increased surface tension, and reduction of air flow resulting from an inflammatory response thereto.

U.S. patent application Ser. No. 09/450,884, the entire disclosure of which is hereby incorporated by reference, discloses a composition and method especially formulated and adapted to increase and enhance mammalian eustachian tube lumen patency and pressure equalization performance by dramatically decreasing the surface tension of the lumenal surface of the eustachian tube. In the method and composition disclosed therein, a mixture of one or more lipids and one or more spreading agents selected from the group consisting of cholesteryl esters, phospholipids, carbohydrates, and proteins, all in powder form, and one or more fluorocarbon propellants is prepared. The lipids and the spreading agents are advantageously selected to be insoluble in the propellants. The lipids utilized in practicing said method are present in an amount of about 80 to 99.5 percent by weight and the spreading agents are present in an amount of about 0.5 to about 20 percent by weight, both based upon the total weight of the mixture. Combination of the one or more lipids, one or more spreading agents and one or more fluorocarbon propellants results in the formation of lipid crystals and described in more detail, below. A metered dose of the mixture of lipid crystals is then administered, via an external nasal orifice into a mammal upon which the present method is practiced.

Upon administration, the propellant(s) are evaporated from the mixture and the lipid crystals are deposited at a nasopharyngeal, or as it may also be described, an anterior terminus, of a subject mammalian eustachian tube whereupon said lipid crystals come into contact with lumen surfaces of the tube. Upon contact with lumen surface tissue and air/liquid interfaces of the eustachian tube lumen, the mixture of lipid crystals forms an amorphous spread film upon said air/liquid interface effectively decreasing the opening pressure thereof.

The lipid crystals deposited upon the lumen surfaces and air/liquid interface thereupon is comprised of one or more lipids which are advantageously selected to demonstrate powerful surfactant activity. In addition, the spreading agent combined therewith provides complete and uniform distribution of the surfactant over and upon the lumen air/liquid surface resulting in substantial decreases in lumen opening pressure. In turn, the decrease in lumen opening pressure results in greater patency of the eustachian tube and thereby providing a resultant increase in fluid conduction/equalizing function of this anatomical structure.

Administration of the aerosolized lipid crystals through the nasal orifice also results in deposition of said crystals upon the mucosal surfaces of the sinus passages and sinus airways. The mucosal surfaces of these airways and sinuses also demonstrates an air/liquid interface formed by the secretion of muco and muco-serous secretions thereupon. Upon deposition of the lipid crystals upon these mucosal surfaces, said crystals form a uniform and amorphous spread film and effectively reduce the surface tension thereupon. Therefore, said method and composition also contemplates reduction of the surface tension of the air/liquid surfaces resident upon mammalian sinus and sinus air way mucosal surfaces.

In a second preferred embodiment of the invention disclosed in U.S. patent application Ser. No. 09/450,884, a method of administering therapeutically active agents, effective in the treatment of otitis media, directly to mammalian eustachian tube and middle ear target tissues is disclosed. In the method of the second embodiment of said invention, a mixture of one or more lipids, one or more spreading agents, one or more therapeutically active agent(s), effective in the treatment of otitis media, and one or more fluorocarbon propellants is prepared. The one or more lipids and spreading agents are advantageously selected from the group consisting of cholesteryl esters, phospholipids, carbohydrates, and proteins, all being in powder form. The one or more lipids, spreading agents and therapeutically active agent(s), effective in the treatment of otitis media, are also advantageously selected to be insoluble in the propellants. In practicing the method of the second embodiment of the invention disclosed therein, the lipids are present in an amount of about 80 to 99.5 percent by weight and the spreading agents are present in an amount of about 0.5 to about 20 percent by weight, both based upon the total weight of said mixture. The mixture resulting from the combination of lipid(s) spreading agent(s) and therapeutically active agent and propellant forms lipid crystals which act as carriers for said therapeutically active agent. A metered dose of the mixture of lipid crystals is then administered, via an external nasal orifice, into a mammal upon which the method is practiced. A suitable bottle equipped with a metered dose valve and nasal administration adaptor is advantageously utilized for this purpose.

Upon administration of the lipid crystal mixture, the propellants, carry the lipid crystals in combination with therapeutically active agent(s) effective in the treatment of otitis media to the nasopharyngeal terminus of the eustachian tube whereupon the propellant(s) evaporate. The lipid crystals and therapeutically active agent is then deposited upon the tissues of the eustachian tube including the epithelial lined lumen whereupon the mixture forms an amorphous spread film effectively carrying said therapeutically active agent effective in the treatment of otitis media uniformly through the eustachian tube and to target tissues of the middle ear. Therefore, said composition and method are disclosed and provides for the administration of therapeutically active agents directly to lumen surfaces of mammalian eustachian tubes, and also, by means of said eustachian tube lumen, to middle ear target tissues wherein said therapeutically active agents provide effective treatment for otitis media while, in addition, providing the same increased eustachian tube patency and performance as the first embodiment.

Although the above-described therapeutic agents useful in treating the disorders causative of upper respiratory inflammation may have undesirable side effects, such effects, systemic in nature, may be reduced by application of reduced amounts of such agents directly to the effected tissues of the upper respiratory system. Thus, such therapeutics, administered via nasal inhalation, may be utilized to place the maximum amount of agent on the target tissue while minimizing systemic exposure. However, it has heretofore not been possible to ensure that such medication, delivered via oral or nasal inhalation, was delivered and distributed uniformly upon the epithelial surfaces of the upper respiratory system or delivered with a carrier capable of significantly reducing the above-described increased surface tension without the use of additional drugs. What is needed is a compound and method wherein a carrier is provided capable of providing direct and uniform application of therapeutically active agents effective in the treatment of upper respiratory inflammation, as well as the disorders causative thereof, directly to epithelial lining of the upper respiratory system, while, independently of said agents, providing a decrease in upper respiratory air flow resistance therethrough by means of powerful surfactant effect.

SUMMARY OF THE INVENTION

Now, in accordance with the present invention, a method of increasing and enhancing air flow through the mammalian upper respiratory system is disclosed wherein high surface tension resulting from viscous mucous resident upon the epithelial lining of upper respiratory air ways and air spaces is substantially reduced so as to promote the opening of said air ways and air spaces for facilitation of respiration therethrough.

In the first preferred embodiment of the present invention, a mixture of one or more lipids and one or more spreading agents selected from the group consisting of cholesteryl esters, phospholipids, carbohydrates and proteins, all in powder form, and one or more fluorocarbon propellants is prepared. The lipids and spreading agents are advantageously selected to be insoluble in the propellants. The lipids utilized in practicing the method of the present invention are present in an amount of about 80 to 99.5 percent by weight and the spreading agents are present in an amount of about 0.5 to about 20 percent by weight, both based upon the total weight of the mixture. Combination of the one or more lipids, or one or more spreading agents and one or more fluorocarbon propellants results in the formation of lipid crystals and described in more detail, below. A metered dose of the mixture of lipid crystals is then administered, via nasal or oral inhalation, into the upper respiratory system of a mammal upon which the present method is practiced.

Upon administration, the propellant(s) are evaporated from the mixture and the lipid crystals are deposited upon the air/liquid interface resident upon the epithelial lining of the air ways and air spaces of the upper respiratory system whereupon said lipid crystals form an amorphous spread film thereupon so as to effectively decrease the surface tension thereof, open and increase the volume thereof so as to decrease resistance to air flow therethrough.

The lipid crystals deposited upon the epithelial surfaces lining the upper respiratory system and air/liquid interface thereupon is comprised of one or more lipids which are advantageously selected to demonstrate powerful surfactant activity. In addition, the spreading agent combined therewith provide complete and uniform distribution of the surfactant over and upon the air/liquid surface resident upon said lining. In turn, the decrease in surface tension afforded thereby tends to separate proximal epithelial lining adherent, one upon the other, so as to increase air way and air space volume and to decrease air flow resistance. In addition, said decrease in surface tension also minimizes and, in some instances, eliminates the collection of fluids therewithin which might otherwise also serve to occlude, or partially occlude said air ways and air spaces. Administration of the aerosolized lipid crystals through nasal or oral inhalation results in deposition of said crystals upon the mucosal surfaces of entire upper respiratory system including the sinus passages and sinus airways.

In a second preferred embodiment of the present invention, a method of administering therapeutically active agents effective in the treatment of upper respiratory congestion and inflammation as well as those agents effective in the treatment of disorders causative thereof—directly to the upper respiratory epithelial lining—is disclosed. In the method of the second embodiment of the present invention, a mixture of one or more lipids, one or more spreading agents, one or more therapeutically active agent(s), effective in the treatment of upper respiratory airway inflammation, and/or the underlying cause thereof and one or more fluorocarbon propellants is prepared. The one or more lipid and spreading agents are advantageously selected from the group consisting of cholesteryl esters, phospholipids, carbohydrates and proteins, all being in powder form. The one or more lipids spreading agents and therapeutically active agent(s), effective in the treatment of said airway restriction, are also advantageously selected to be insoluble in the propellants. In practicing the method of the second embodiment of the present invention, the lipids are present in an amount of about 80 to 99.5 percent by weight and the spreading agents are present in an amount of 0.5 to 20 percent by weight, both based upon the total weight of said mixture. The mixture resulting from the combination of lipid(s) and spreading agent(s) and therapeutically active agents and propellant forms lipid crystals which act as carriers for said therapeutically active agents. A metered dose of the mixture of lipid crystals is then administered via nasal or oral inhalation, into the upper respiratory system of a mammal upon which the method is practiced. A suitable bottle equipped with a metered dose valve and nasal or oral administration adaptor is advantageously utilized for this purpose.

Upon administration of the lipid crystal mixture, the propellants, carry the lipid crystals in combination with therapeutically active agent(s) effective in the treatment of upper respiratory inflammation as well as those agents effective in the treatment of the underlying causes thereof, directly to, and uniformly upon the epithelial lining of the upper respiratory system. The lipid crystals and therapeutically active agent(s) are then deposited upon the epithelial tissue lining of the upper respiratory system whereupon the mixture forms an amorphous spread film effectively carrying said therapeutically active agent effective in the treatment of upper respiratory inflammation and/or the underlying cause thereof, uniformly therethrough and thereupon.

As stated in further detail below, the therapeutically active agent is advantageously selected to be effective in the treatment of upper respiratory inflammation as well as agents effective in the treatment of the underlying causes of said immune responses leading to the above-described inflammatory responses. For example, such agents may be selected to be effective in the treatment of viral or bacterial infections, (as well as combinations thereof) underlying and causative of said inflammatory reactions. Therefore, the second preferred method of the present invention provides a method of administering therapeutically active agents directly to the epithelial lining of the upper respiratory system wherein said therapeutically active agents provide effective treatment for the subject inflammatory condition such as, for example edema—as well as the underlying causes thereof—while, simultaneously, the mixture of lipid crystals acts to directly and effectively open the air ways and air spaces by decreasing the surface tension of the viscous mucous exudate thereupon.

The lipid crystals deposited upon the air/liquid interface of said epithelial surfaces lining the upper respiratory system and the air/liquid interface resident thereupon is comprised of one or more lipids which are advantageously selected to demonstrate powerful surfactant activity and to serve as a carrier for selected therapeutic agent(s). In addition, the spreading agent deposited therewith provides complete and uniform distribution of the surfactant and therapeutic agent (s) throughout the lining of the upper respiratory system resulting in substantial decreases in air way resistance.

Administration of the lipid crystals through nasal or oral inhalation results in effective deposition of said crystals uniformly upon the epithelial mucosa of the entire upper respiratory system. Such deposition effectively decreases the surface tension of said surfaces. In those instances where, as discussed above, the increased surface tension and proximal airway swelling associated with upper respiratory inflammation and congestion has caused partial obstruction of the upper respiratory tract, the surface tension lowering properties of the lipid crystals acts to promote separation of proximal walls resulting in increased airway volume and a decrease to air flow resistance. In those embodiments of the present invention wherein delivery of therapeutically active agents to the upper respiratory system is provided, said agents are selected to be effective in the treatment of the disorder underlying and leading to an upper respiratory inflammation. It is contemplated that such disorders may be of a microbial, for example, a viral, protozoic, bacterial, fungal; or non-microbial, such as, for example, particulate or toxic/irritant chemical origin.

In some instances, more than one such agent may be carried by means of the lipid crystals to the upper respiratory mucosa. Such agents are contemplated to be antibiotics, antiviral agents, anti-inflammatory agents (steroid and non-steroid) anti-histamines and decongestants as well as combinations thereof.

The lipids utilized in practicing the method of the present invention may be advantageously selected to be phospholipids, neutral lipids or mixtures thereof. The phospholipids utilized may be further advantageously selected to be any phospholipid of the class known as phosphatidlycholine including any fully saturated diacyl phosphatidlycholine including 1,2 dipalmitoyl phosphatidylcholine (DPPC); a diacylphosphatidylglycerol; a diacylphosphatidylethanolamine; a diacylphosphatidylserine; a diacylphosphatidylinositol; sphingomyelin, Cardiolipin, lysophospholipid; a plasmalogen; a diether phosphonolipid; or a dialklyphospholipid.

The cholesteryl esters utilized in practicing the method of the present invention may be advantageously selected to be cholesteryl palmitate, cholesteryl oleate or cholesteryl stearate. Carbohydrates utilized in the present invention may be advantageously selected to be glucose, fructose, galactose, pneumogalactan, or dextrose. Proteins especially suited and advantageously selected for use in the present invention include albumin, pulmonary surfactant specific proteins A or B or C or D, their synthetic analogs, and mixtures thereof.

The fluorocarbon propellants may be advantageously selected to be chlorofluorocarbon propellants, hydrofluorocarbons or mixtures thereof. In addition, the present invention contemplates carbon dioxide as a suitable propellant. The mixture is advantageously prepared to yield crystalline forms that demonstrate a particle size equal to or less than 16 microns in diameter. The diminutive nature of the crystalline particles is, as discussed in detail below, highly advantageous in enabling dispersion and application of the aerosolized mixture.

The therapeutically active agent(s) referred to throughout this disclosure and in the claims refer to those agents, discussed in detail below that effectively reduce or eliminate the subject inflammatory effects as well as agents that treat the underlying precipitating factors thereof as discussed here-above and hereafter.

DETAILED DESCRIPTION OF THE INVENTION

Throughout the specification and claims, the phrase "therapeutically active agent" includes any substance which is capable of altering a biologic, physiologic and/or immunologic function, in nature or degree and includes those substances generally referred to as pharmacologic agents and drugs, including nucleic acids utilized in gene therapy, in order to provide treatment of the symptoms or underlying causes of the subject inflammation; the term "fluorocarbons" includes the class of both chlorofluorocarbons and, hydrofluorocarbons; the term "lipids" includes the class of phospholipids including, but not limited to PC, PG, PE, PI and Cardiolipin; and the phrase "spreading agent(s)" refer to and includes PG, PE, PS, PI, Sph., Card., lysophospholipids, plasmalogens, dialkylphospholipids, and all others in the class phospholipid as well as cholesteryl esters (like CP), proteins and carbohydrates.

Throughout this specification and claims, the phrase "spreading agent(s)" refers to compounds, as listed above, which assist the one or more lipid such as, for example, DPPC, in rapidly adsorbing and forming an amorphous spread film on air/liquid interfaces such as that found upon the epithelial lined lumen of the auditory tube. In addition, the compounds referred to as "spreading agent(s)", together with the one or more lipids, are responsible for achieving and maintaining biophysical properties including, but not limited to, reduction of intermolecular attractive forces, surface tension, and the resultant attractive forces generated thereby, that tend to cause opposed surfaces, such as the lateral and medial epithelial lined lumen walls of the auditory tube, to adhere to each other.

The major lipid component utilized in practicing a preferred embodiment of the present invention is advantageously selected to be phospholipid 1,2 dipalmitoyl, phosphatidlycholine (DPPC). DPPC is the most surface active of the phospholipids or any of the subclass of fully saturated acyl chain phospholipids. That is to say that DPPC, in combination with any spreading agent(s) disclosed herein, has a maximum effect in reducing surface tension at an air/liquid interface.

Another, minor lipid component that also acts as a spreading agent for the major component is advantageously selected to be diacylphosphatidylglycerol (PG). The number of carbon atoms in the acyl chains R and R', (see PG formula below) can vary between 8 and 22 and may or may not be fully saturated. DPPC and PG can be synthesized. However, since DPPC and PG are the main phospholipid constituents of cells, they are also readily extractable from such cells by non-polar solvents, i.e., chloroform, ether, acetone. DPPC's structural formula is:

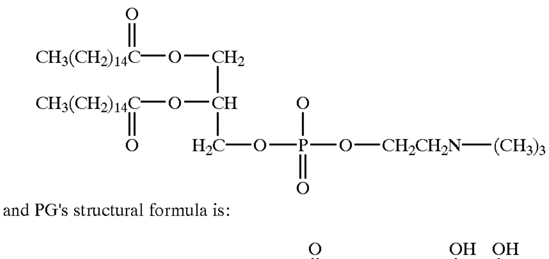

and PG's structural formula is:

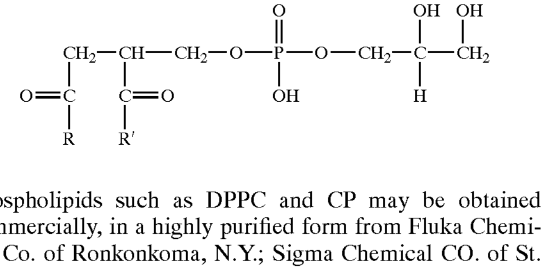

Phospholipids such as DPPC and CP may be obtained commercially, in a highly purified form from Fluka Chemical Co. of Ronkonkoma, N.Y.; Sigma Chemical CO. of St. Louis Mo.; and Avanti Polar Lipids of Birmingham, Ala. and Primedica of Cambridge, Mass.

DPPC and PG are preferred component(s) advantageously utilized in the present inventions methods for administering therapeutically active agents to the middle ear and auditory tube. In addition, these lipids increase the pressure equalizing performance of the auditory tube by direct result of their surfactant qualities. DPPC may be selected to be present in the composition over a fairly wide range. Percentages of DPPC may be s as low as 70% and as high as 99.5% of the lipids by weight with little change in the in-vitro properties, and the effectiveness of the present method. However, 99.5% DPPC by weight is selected for the preferred embodiment.

Throughout this disclosure and within the claims, the terms "reducing resistance to air flow," reducing airway resistance," and "improving air flow" singly, in combination and interchangeably all refer to the reduction of the force required to enable inspiratory and expiratory air through the air spaces and air ways of the upper respiratory system. The resistance referred to results from: reduction of the volume, partial obstruction, or complete occlusion of the upper respiratory airways and air spaces by swelling of the epithelium lining thereof; reduction of the volume, partial obstruction or complete obstruction of said air ways and air spaces by secretions resident upon said epithelial lining; and reduction of the volume, partial obstruction or complete obstruction of said air ways and air spaces by fluids collecting therewithin resulting from the effects of an immune response. In those embodiments of the present invention wherein the aerosolized mixture of lipid crystals does not include, or act as a carrier for, a therapeutically active agent(s), the above-described reduction in resistance to air flow is brought about by the separation of proximal upper respiratory epithelial surfaces by means of decreasing the surface tension thereupon. The term "proximal upper respiratory epithelial surfaces" as utilized throughout this specification and throughout the claims, refers to portions of the epithelial surface, lining the upper respiratory air ways and air spaces which, due to close proximity and/or opposition to each other, may come into contact as the result of, for example, epithelial or sub-epithelial edema, excess surface secretions, high surface tension, high negative air pressure or any combination thereof.

In those instances where the aerosolized mixture of lipid crystals does include and act as a carrier for a therapeutically active agent(s), the above-described reduction in resistance to air flow is brought about by: lowering the surface tension of proximal epithelial walls of and decreasing the pooling of secretions within said air ways and air spaces by means of said lipid crystals; and by reducing or temporarily halting the inflammatory response causing the edema, and excess viscous secretions by i. direct anti-inflammatory effect, ii by treating the triggering factor of said inflammation, or iii. by combinations thereof.

For example, in those instances of the present invention wherein an anti-histamine is the therapeutically active agent, proximal walls of epithelial mucosa lined air ways of the upper respiratory system that are adherent to each other are separated and opened by means of both lipid crystal mediated reduction of surface tension and, upon action of said anti-histamine, reduction of edema, reduction of mucous volume, and decrease in the viscous nature thereof.

Another lipid that can be utilized in practicing the methods of the present invention is cholesteryl palmitate( CP), which also serves as a spreading agent. This cholesteryl ester is a neutral lipid which belongs to a class of organic compounds that are also cell constituents and are extractable by non-polar solvents such as chloroform, methanol, ether, etc. The structural formula of CP is:

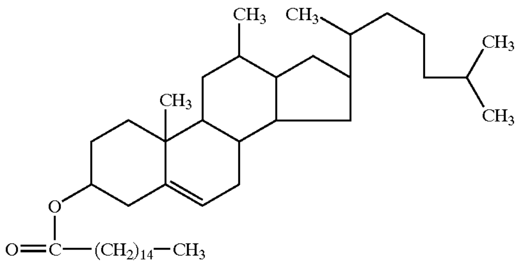

CP may be obtained commercially in a highly purified form from Fluka Chemical Co. and Sigma Chemical Co and Primedica. The CP component constitutes a minor portion of the composition, since it is selected to be present in an amount ranging from 0.5% to 10% by weight. Also, the preferred ratio of DPPC to CP is 99.5 DPPC to 0.5 CP by weight. However, the percentages may be altered within that range without undue interference in desired properties needed for drug delivery and surfactant activity.

The term "therapeutically active agents effective in the treatment of upper respiratory inflammation" as utilized in and throughout this specification and claims, refers to those drugs effective in direct treatment of the inflammatory response causing the above-described air way and air space resistance as well as those drugs effective in the treatment of the underlying or precipitating cause of such inflammation such as, for example: treatment of infection, of microbial origin, such as, for example, viral, protozoic, bacterial, fungal and/or parasitic origin-; treatment of non-microbial allergic response resulting from antigenic matter such as, for instance, particulate (e.g. pollens and dust) and chemical triggers; as well as treatment of autoimmune disease causative of such inflammation. Therefore, it is contemplated that embodiments of the present invention may include as a therapeutic agent, singly or in combination: drugs effective in the direct treatment of the subject inflammation such as, for example, corticosteroids including, for example, betamethasone, including, for example, betamethasone dipropionate and betamethasone valerate as well as all other effective formulations; de-congestive agents such as phenylephrine, including, for example, phenylephrine HCL and phenylephrine bitartrate and all other effective formulations thereof; anti-viral agents such as, for example zovirax; and antibiotics including, for example erythromycin, amoxicillin, zythromax, and augmentin (amoxicillin and clavuliic acid) in all of their effective formulations. The term "all of their effective formulations" as used throughout this specification and in the claims refers to those specific species of a particular therapeutic agent effective in the treatment of the above-described upper respiratory do. It is also contemplated that said therapeutically effective agents include nucleic acids as well as the vectors thereof as utilized in gene therapy.

The combination of lipid component(s) and spreading agent component(s) disclosed herein, may be referred to, collectively, as the "carrier" when said combination is mixed with a therapeutically active agent so as to act as a carrier therefore. When practicing the method of the present invention wherein therapeutically active agents are administered directly to the epithelial lining of the upper respiratory system, it is preferred that carrier, the mixture of one or more lipids and one or more spreading agents, be comprised of a mixture of DPPC and CP in a 200:1 ratio (by weight). However, it has been found that a ratio range of from 5:1 to 300:1 (DPPC/CP) will also produce an effective carrier for this embodiment. If, for example, the therapeutic agent is selected to be betamethasone, the weight ratio of betamethasone to carrier (DPPC/CP) is advantageously selected to be 1 microgram betamethasone to 5 milligrams carrier. However, it has been found that a weight ratio range of 0.5 to 1000 micrograms betamethasone/5 milligrams carrier yields an effective and functional mixture.

When practicing the method of the present invention wherein the therapeutically active agent is selected to be phenylephrine it is preferred to select the weight ratio of phenylephrine to carrier to be 160 micrograms/995 milligrams. However, it has also been found that a weight ratio range of from 50 to 5000 micrograms (phenylephrine): 995 to 900 milligrams carrier, respectively, forms an effective mixture and functional mixture. The term "effective and functional mixture" as utilized throughout this application and in the claims refers to the effectiveness of the mixture of lipid crystals in combination with said therapeutically active agent resulting from the combinations disclosed herein in: (a) reaching the target tissue of the epithelium of the upper respiratory system; (b) reducing the surface tension thereupon; and (c) delivering a uniform dose of therapeutic agent directly to and spreading uniformly upon and throughout the epithelium lining the upper respiratory tract so as to effectively bring symptomatic relief and/or resolution of the afore-mentioned pathological conditions underlying upper respiratory inflammation as well as acting, by means of said lipid crystals to open the air ways and air spaces by reduction of surface tension and elimination of pooled fluids.

When practicing the method of the present invention wherein the therapeutically active agent is selected to be the antibiotic erythromycin, the ratio of erythromycin to carrier is advantageously selected to be 200 mg antibiotic to 800 mg carrier (DPPC/CP) by weight. However, a weight range of from 50 to 200 mg erythromycin: from 950 to 800 mg carrier, respectively, has been found to be fully effective in practicing the present method.

The fluorocarbon propellants utilized in practicing the method of the present invention, namely: trichlorodifluoromethane, dichlorodifluoromethane, and tetrafluoromethane or mixtures thereof, which are commercially available from Union Carbide Corp., Danbury, Conn. and Armstrong Laboratories, West Roxbury Mass. are advantageously selected for formation of the lipid crystalline figures of the present invention. The fluorocarbon propellants are present over a range of 2 to 30 times the amount, by weight, of lipid, but components of lipid and fluorocarbon propellants both are needed in order to obtain the required lipid crystalline figures.

In practicing the methods of the present invention wherein therapeutically effective agents are administered directly to the epithelial tissue lining the upper respiratory tract, DPPC is advantageously selected as the major lipid component since the amphoteric nature of this phospholipid allows the molecule to act as a carrier for any drug or therapeutic agent. However, the presence of a charge on other lipid components (a negative charge on PG, for example) would alter and further improve the carrying capacity of the lipid crystals for a particular therapeutic agent.

In addition to erythromycin and amoxicillin, the method of the present invention also contemplates selecting zythromax and Augmentin (amoxicillin+clavulinic acid) as antibiotic therapeutic agents and zovirax as an anti-viral agent.

However, because of the highly amphoteric nature of the carrier utilized herein, the use of any presently known and available, as well as anti-viral, antibiotic or gene therapy developed in the future capable of providing effective treatment of infections of the upper respiratory tract are contemplated and fully functional with the methods and compositions herein.

EXAMPLE 1

The aerosolized drug delivery system of the present invention was prepared from chromatographically pure (greater than 99%) DPPC and CP. Both materials were purchased from suppliers on the commercial market where they are available from several chemical supply houses. Specifically, the DPPC and CP were purchased from Sigma Chem., St Louis, Mo. All purchased materials were checked for purity by standard chromatographic analysis. The betamethasone utilized in this example was also purchased from Sigma Chemical. The DPPC and CP were then mixed in the dry powder form in a weight ratio of 200:1 (DPPC:CP). To 5 milligrams of the resultant carrier, 1 microgram of betamethasone was added in order to yield a weight ratio of 5000:1 (carrier: betamethasone). Then 5 grams of this mixture was suspended in 55 grams of the first propellant, trichloromonofluoromethane (P11) and subdivided into 30 ml. Wheaton plastic-coated glass bottles with a 20 mm neck finish. Valois metered dose valves were then crimped onto each bottle through which 40 gms of the second propellant, dichlorodifluoromethane (P12), was passed. The filled bottles were then gently shaken to disperse the solids that are insoluble in the propellants. The bottles were thereafter immersed in a water bath to test for leaks and then fitted with a nasal administration adapter. The suspension was homogenous. After standing at room temperature for about three days, a pellicle forms on top of the propellants but is easily re-suspended by gentle shaking. The size of the metering valve can be varied to deliver from 1 mg up to 5.4 mg of the DPPC:CP:Betamethasone aerosolized mixture. However, metered dose valves having a greater dosing range are also contemplated and can be utilized in other embodiments of the present invention.

EXAMPLE II

The aerosolized drug delivery system of the present invention was prepared from chromatographically pure (greater than 99%) DPPC and CP. Both materials were purchased from suppliers on the commercial market where they are available from several chemical supply houses. Specifically, the DPPC and CP were purchased from Sigma Chem., St Louis, Mo. The phenylephrine utilized in this example can also be purchased from Sigma Chem., St Louis, Mo. All purchased materials were checked for purity by standard chromatographic analysis. The DPPC and CP were then mixed in the dry powder form in a weight ratio of 200:1 (DPPC:CP). Thereafter, to 995 milligrams of the resultant carrier, 160 micrograms of phenylephrine was added so as to yield an approximate 6200:1 weight ratio of carrier to phenylephrine. Then 5 grams of the resultant mixture (DPPC/CP/phenylephrine) was suspended in 55 grams of the first propellant, trichloromonofluoromethane (P11) and subdivided into 30 ml. Wheaton plastic-coated glass bottles with a 20 mm neck finish. Valois metered dose valves were then crimped onto each bottle through which 40 gms of the second propellant, dichlorodifluoromethane (P12), was passed. The filled bottles were then gently shaken to disperse the solids that are insoluble in the propellants and nasal administration adaptors. The bottles were immersed in a water bath to test for leaks and then fitted with a nasal administration adapter. The suspension was homogenous. After standing at room temperature for about three days, a pellicle forms on top of the propellants but is easily re-suspended by gentle shaking. The size of the metering valve can be varied to deliver from 1 mg up to 5.4 mg of the DPPC:CP: phenylephrine aerosolized mixture. However, metered dose valves having a greater dosing range are also contemplated and can be advantageously utilized in practicing the methods of the present invention.

EXAMPLE III

The aerosolized drug delivery system of the present invention was prepared from chromatographically pure (greater than 99%) DPPC and CP. Both materials were purchased from suppliers on the commercial market where they are available from several chemical supply houses. Specifically, the DPPC and CP were purchased from Sigma Chem., St Louis, Mo. The erythromycin utilized in this example can also be purchased from Sigma Chem., St Louis, Mo. All purchased materials were checked for purity by standard chromatographic analysis. The DPPC and CP were then mixed in the dry powder form in a weight ratio of 200:1 (DPPC:CP). Thereafter, to 800 milligrams of the resultant carrier, 200 milligrams of erythromycin was added so as to yield an approximate 4:1 weight ratio of carrier to erythromycin. Then 5 grams of the resultant mixture (DPPC/CP/erythromycin) was suspended in 55 grams of the first propellant, trichloromonofluoromethane (P11) and subdivided into 30 ml. Wheaton plastic-coated glass bottles with a 20 mm neck finish. Valois metered dose valves were then crimped onto each bottle through which 40 gms of the second propellant, dichlorodifluoromethane (P12), was passed. The filled bottles were then gently shaken to disperse the solids that are insoluble in the propellants. The bottles were immersed in a water bath to test for leaks and then fitted with a nasal administration adapter. The suspension was homogenous. After standing at room temperature for about three days, a pellicle forms on top of the propellants but is easily re-suspended by gentle shaking. The size of the metering valve can be varied to deliver from 1 mg up to 5.4 mg of the DPPC:CP:erythromycin aerosolized mixture. However, metered dose valves having a greater dosing range are also contemplated and can be advantageously utilized in practicing the methods of the present invention.

EXAMPLE IV

The aerosolized drug delivery system of the present invention was prepared from chromatographically pure (greater than 99%) DPPC, PG and CP. All of these materials were purchased from suppliers on the commercial market where they are available from several chemical supply houses. Specifically, the DPPC, CP and PG were purchased from Sigma Chem., St Louis, Mo. The erythromycin utilized in this example can also be purchased from Sigma Chem. All purchased materials were checked for purity by standard chromatographic analysis. The DPPC, PG and CP were then mixed in the dry powder form in a weight ratio of 7:1:0.35 (DPPC:PG:CP). Thereafter, to 800 milligrams of the resultant carrier, 200 milligrams of erythromycin was added so as to yield an approximate 4:1 weight ratio of carrier to erythromycin. Then 5 grams of this mixture was suspended in 55 grams of the first propellant, trichloromonofluoromethane (P11) and subdivided into 30 ml. Wheaton plastic-coated glass bottles with a 20 mm neck finish. Valois metering valves were crimped onto each bottle through which 40 gms of the second propellant, dichlorodifluoromethane (P12), was passed. The filled bottles were then gently shaken to disperse the solids that are insoluble in the propellants. The bottles were thereafter immersed in a water bath to test for leaks and then fitted with a nasal administration adapter. The suspension was homogenous. After standing at room temperature for about three days, a pellicle forms on top of the propellants but was easily resuspended by gentle shaking. The size of the metering valve can be varied to deliver from 1 mg up to 5.4 mg of the DPPC:PG:CP:erythromycin aerosolized mixture.

EXAMPLE V

Chromatographically pure DPPC and CP (99% pure) were obtained from Avanti Polar Lipids Co. of Birmingham, Ala. and Sigma Chemical Co. of St. Louis, Mo.

DPPC and CP were mixed in a weight ratio of 200:1 (DPPC:CP). Then 5 grams of this mixture was suspended in 55 grams of the first propellant, trichloromonofluoromethane (P11) and subdivided into 30 ml. Wheaton plastic-coated glass bottles with a 20 mm neck finish. Valois metering valves were crimped onto each bottle through which 40 gms of the second propellant, dichlorodifluoromethane (P12), was passed. The filled bottles were then gently shaken to disperse the solids that are insoluble in the propellants. The bottles were thereafter immersed in a water bath to test for leaks and then fitted with a nasal inhalation adapter. The suspension was homogenous. After standing at room temperature for about three days, a pellicle forms on top of the propellants but was easily re-suspended by gentle shaking. The size of the metering valve can be varied to deliver from 1 mg up to 5.4 mg of the DPPC:CP aerosolized mixture.

The afore-described Examples "I" through "IV" are specific embodiments of the aerosolized drug delivery system utilized in practicing the method of the present invention. Each of the afore-mentioned Examples "I" through "IV" are administered by releasing a metered dose of the mixtures, by means of a nasal administration adaptor, through the nose. The aerosolized mixture, propelled by the above-described propellants, is then deposited uniformly throughout the epithelium of the upper respiratory system. When the crystalline lipid figures come in contact with the epithelial surface lining the upper respiratory system, an amorphous spread film layer forms upon the air/liquid interface resident thereupon. Upon such contact, said mixture of lipid crystals by means of the afore-mentioned surfactant properties, substantially lowers the surface tension of said air/liquid interface so as to allow the afore-mentioned opening of said air ways and air spaces and elimination of pooled liquid obstructions thereof.

In the above-described Example "I", wherein the therapeutically active agent is the anti-inflammatory, betamethasone, the agent acts directly upon the inflammatory process itself occurring within the upper respiratory epithelium, reducing the production of the afore-mentioned excess and viscous mucoid secretions while also decreasing tissue edema. Both excess mucoid secretions and edema act to reduce upper respiratory air flow since both of these factors tends to reduce air way and air way volume by reducing, partially obstructing, or totally occluding such air ways. Reduction in air way space likewise results in an increased effort necessary in order to move air through the upper respiratory system during inspiration and expiration. Thus, therapeutic agents of anti-inflammatory activity reduce air way and air space resistance by increasing conduit volume. However, in addition to such action of anti-inflammatory agents, the DPPC and/or DPPC/PG lipids of the present invention act independently of selected therapeutic agent(s) in promoting the opening of air ways and air spaces by reduction of the surface tension of the epithelial lining—by reducing the intermolecular and surface charges found at the air/interface of the viscous secretion covered lumen—. Thus, DPPC and/or DPPC/PG lipids of the present invention are able to open air ways and air spaces of the upper respiratory system independent of the action of therapeutic agents carried thereby.

The present invention also contemplates the use of antibiotics such as, for example, erythromycin (Example "III" and "IV"), amoxicillin, zythromax and augmentin (amoxicillin+clavulinic acid) as well an anti-viral agents. In such embodiments, the DPPC and/or DPPC/PG act to introduce such drugs in the upper respiratory epithelium in the same manner as described immediately above in regards to anti-inflammatory agents. Such anti-biotic and anti-viral agents act indirectly upon the inflammatory process provoked by the presence of antigenic microbial proteins by acting to reduce or eliminate the presence thereof. As the antigenic challenge of such microbes is reduced by the action of such therapeutic agents, the degree and intensity of inflammation—edema and excess viscous mucous—is reduced. However, while DPPC and DPPC/PG aerosolized mixtures act as carriers for such drugs, they also continue to provide the independent and more expeditiously effect on air way and air space resistance discussed above by effecting a substantial decrease in surface tension of the air/liquid interface resident upon the upper respiratory epithelium—on contact—. Therefore, in instances in which the method of the present invention is utilized to treat an underlying microbial infection of the upper respiratory system, direct application of antibiotic therapy to the target tissues is accomplished, leading to diminished microbial activity or death. Such anti-microbial effect indirectly reduces the increased air way and air space resistance of the upper respiratory system caused by inflammatory response thereto by reducing and/or eliminating the presence of such antigenic proteins.

In Example "V", above, preparation of an aerosolized mixture of lipid crystals for use in practicing the method of the present invention is disclosed that is advantageously formulated for decreasing upper respiratory air way and air space resistance without the use of a therapeutically active agent. In practicing the second preferred embodiment of the present invention, the aerosolized mixture, propelled by the above-described propellants, is deposited uniformly upon the air/liquid interface resident upon the epithelial lining of the upper respiratory system. Upon contact of the crystalline lipid figures with the air/liquid interface, an amorphous spread film layer if formed thereupon, uniformly spreading throughout said air spaces and air ways. Upon contact with the air/liquid interface, the increased surface tensions thereof—associated with upper respiratory inflammation and discussed in great detail above—is substantially reduced. The reduction of said surface tension effects an opening of the air ways and air spaces of the upper respiratory system by releasing adherent or partially adherent proximal and/or opposing epithelial surfaces, lining said air ways and air spaces—from adhesion, one to another as well as reducing pooled fluids blocking or partially blocking said air spaces and air ways. In this example, no therapeutically active agent is included in the aerosolized mixture or contemplated in this embodiment. Increased air way and air space patency is provided by means of interaction of the surfactant/spreading agent combination alone. In many instances, especially in the absence of underlying infection embodiments of the present invention not incorporating therapeutically active agents may be preferred so as to control respiratory inflammation while minimizing systemic effects inherent in the use of many of such agents.

Structural Characteristics

Particle Size and Gross Configuration

Particle size of the nebulized crystals produced and utilized in practicing the present invention is, as discussed below, critical to effective administration. The size (diameter) of the lipid crystals were therefore determined utilizing in a cascade impactor. Flow through the impactor was adjusted to be substantially identical to the flow from a nebulizer utilized in practicing the disclosed method. All of the lipid crystals were found to have a diameter equal to or less than 16 microns. The diameter of about 95 percent of the particles were found to be equal to or less than 4 microns in diameter. Of the particles found to be 4 microns or less, half were, in fact, 1 micron in diameter. The mean diameter demonstrated by the lipid crystals utilized in the method of the present invention was 1.75+/−0.25 microns.

Micronization may be advantageously utilized in order to insure reduced particle size. Therefore, the methods of the present invention also contemplate the use of a micronization mill such as, for example, the "DYNO" mill, type KDL, manufactured by Glen Mills Inc., of New Jersey in the preparation of the aerosolized mixture. For example, approximately 83 grams of CP and 13.33 g of DPPC powder were weighed and transferred to a bead mill within the milling chamber of a DYNO mill (having about 480 cc of glass beads). The chamber was then sealed. Thereafter, 1 liter of HFC-134a was added and the system chilled to about −10° C. at a pressure of approximately 65 psi. Milling was achieved in about 1 hour. Thereafter, the resultant slurry was utilized to fill 5 mil epoxy phenolic lined aluminum cans (Safet Embamet, St. Florantine, France), fitted with Valois metering valves (DFI/ACT/kematal, Valois, Le Neuborg, France with Micron-4 acuators (also Valois). A laser particle sizer, model 2600c, Malvern Instruments, Inc., was thereafter utilized to size the resultant particles as shown in Table "1", below. This data indicates that approximately 90% of the particles emitted fro the valve and actuator system are under 7 $\mu$m or less in diameter. The mean diameter (arithmetic mean) is approximately 5 $\mu$m and the mass median aerodynamic diameter (MMAD) is about 3.4 $\mu$m with a geometric standard deviation (GSD) of about 0.5. Particle size results in physically unstable dispersions should change dramatically over a few days of undisturbed storage.

TABLE 1

| | Particle Size Summary | | | | |
|---|---|---|---|---|---|
| Day Number | 90 Percentile | 50 Percentile | % ≦ 10 $\mu$m | MMAD | GSD |
| 1 | 6.9 $\mu$m | 5.1 $\mu$m | 100 | 3.4 | 0.5 |
| 2 | 6.8 $\mu$m | 4.8 $\mu$m | 99.9 | 3.5 | 0.5 |
| 3 | 7.3 $\mu$m | 5.4 $\mu$m | 100.0 | 3.5 | 0.5 |
| 4 | 6.5 $\mu$m | 4.6 $\mu$m | 99.9 | 3.2 | 0.5 |
| 5 | 6.8 $\mu$m | 4.7 $\mu$m | 100.0 | 3.4 | 0.5 |
| Mean | 6.9 ± 0.3 $\mu$m | 4.9 ± 0.3 $\mu$m | 100.0 | 3.4 ± 0.1 | 0.5 |

Structural characteristics of the mixture of lipid crystals utilized in practicing the present invention were further assessed by capturing the aerosolized particles on standard scanning electron microscopic grids fixed to glass slides at 22° C., (dry). The lipids deposited on glass both as dry particles and as coalesced droplets. The latter evaporated immediately leaving dry lipid. The dry lipids, were fixed in osmium vapor ($O_5O_4$), coated and viewed with a scanning electron microscope. Crystalline figures about 100 angstroms thick, were grouped in clumps on the dry surface. This is a unique configuration.

Crystalline Structure

The mixture of one or more lipids, one or more spreading and one or more fluorocarbon propellants disclosed in the present invention is especially formulated and combined to form a unique crystalline structure with physical dimensions highly advantageous to all embodiments. For example, the crystalline structure results in, as discussed above, a mean particle size of 1.75 microns. The minute physical dimensions of the individual nebulized particles enables the propellant utilized in practicing the present invention to easily and effectively transfer the disclosed mixture to and throughout the desired target tissue. A larger physical configurations such as, for example, a liposome, would not enable such diminutive particle size within and effective physical transport by the propellant.

Functional Properties

The aerosolized mixture of the present invention is crystalline. The crystalline nature of the mixture imparts increased efficiency of particle dispersion within the aerosol mist applied by means of a metered-dose nebulizer. Upon application, the fluorocarbon medium, either chlorofluorocarbon or hydrofluorocarbon, vaporizes rapidly and the DPPC/CP, DPPC/CP drug, DPPC/PG drug or DPPC/PG/CP drug dispersion deposits on an aqueous surface at 37° C., initially in the crystalline form, and then, instantaneously, spreads over the surface as an amorphous surface film. In embodiments wherein a therapeutic is combined with the carrier, the drug likewise is spread, uniformly, upon the aqueous surface.

The surfactant/spreading agent functions and characteristics of the method and composition of the present invention were tested as follows. Aerosolized crystalline figures of the present invention were impacted upon a liquid surface (normal saline solution, NSS) at 37° C., 100% humidity in a surface balance resulted in a rapid spreading of a principally amorphous film that covered the entire surface (18.1 $cm^2$). Surface tension of the film was measured during expansion and compression at 37° C., 100% humidity. Film expansion to 110.4 $cm^2$ produced a surface tension of 72 dynes/cm and compression to 18.1 $cm^2$ lowered surface tension to less than 1 dyne/cm.

The terms and expressions which have been employed in the foregoing specification are used therein as terms of description and not limitation, and there is no intention, in the use of such terms and expressions, of excluding equivalents of the features shown and described or portions thereof, it being recognized that the scope of the invention is defined and limited only by the following claims.

I claim:

1. A method of reducing resistance to air flow through mammalian upper respiratory systems comprising administering a dose of a mixture of lipid crystals, as an aerosol, through an external airway of said mammal, said mixture being comprised of:

a mixture of one or more lipid surfactant and one or more spreading agent, said lipid surfactant and said spreading agent being selected from the group consisting of cholesteryl esters, phospholipids, carbohydrates and proteins, all in powder form; and one or more propellant, wherein said one or more lipid surfactant is present in an amount of from about 80 to 99.5 weight percent and said one or more spreading agent is present in an amount of from about 0.5 to 20 weight percent, based upon the total weight of said mixture, said lipids and said spreading agents being insoluble in the propellants, wherein a mixture of lipid crystals is formed.

2. The method of claim 1 wherein said mixture is administered via nasal inhalation utilizing a metered dose device.

3. The method of claim 1 wherein said aerosolized mixture is administered via oral inhalation utilizing a metered dose device.

4. The method of claim 1 wherein the lipids are phospholipids, neutral lipids or mixtures thereof.

5. The method of claim 4 wherein the phospholipids are any of a class known as phosphatidylcholines.

6. The method of claim 5 wherein the phosphatidylcholine is any fully saturated diacyl phosphatidylcholine.

7. The method of claim 4 wherein the phospholipid is diacylphosphatidylglycerol.

8. The method of claim 4 wherein the phospholipid is diacylphosphatidylethanolamine.

9. The method of claim 4 wherein the phospholipid is diacylphosphatidylserine.

10. The method of claim 4 wherein the phospholipid is diacylphosphatidylinositol.

11. The method of claim 4 wherein the phospholipid is a sphingomyelin.

12. The method of claim 4 wherein the phospholipid is Cardiolipin.

13. The method of claim 4 wherein the phospholipid is a lysophospholipid.

14. The method of claim 4 wherein the phospholipid is plasmalogen.

15. The method of claim 4 wherein the phospholipid is a diether phosphonolipid.

16. The method of claim 4 wherein the phospholipid is a dialkylphospholipid.

17. The method of claim 1 wherein the carbohydrates are glucose, fructose, galactose, pneumogalactan or dextrose.

18. The method of claim 1 wherein the protein is selected from albumin and pulmonary surfactant specific proteins A or B or C or D or mixtures thereof.

19. The method of claim 1 wherein the cholesteryl ester is cholesteryl palmitate, cholesteryl oleate or cholesteryl stearate.

20. The method of claim 1 wherein the propellant is a fluorocarbon, chlorofluorocarbon, hydrofluorocarbon, carbon dioxide or mixtures thereof.

21. The method of claim 1 wherein 95 percent of said lipid crystals demonstrate a particle size no greater than 4 microns in diameter.

22. A method of administering therapeutically active agents, effective in the treatment of upper respiratory disorders, to the epithelial lining of the upper respiratory system while decreasing the resistance to airflow therethrough comprising administering a dose of an aerosolized mixture of lipid crystals in combination with at least one said therapeutically active agent through an external airway of a mammal in need of such treatment, said mixture of lipid crystals in combination with said therapeutic agents comprising:

a mixture of one or more lipid surfactant and one or more spreading agent selected from the group consisting of cholesteryl esters, phospholipids, carbohydrates and proteins, said lipid surfactants and spreading agents all being in powder form; at least one therapeutically active agent effective in the treatment of upper respiratory disorders, and one or more propellants, wherein said at least one lipid surfactant is present in an amount of from about 80 to 99.5 weight percent and said at least one spreading agent is present in an amount of from about 0.5 to about 20 weight percent, based upon the total weight of said mixture, said lipids, said spreading agents and said therapeutically active agents all being insoluble in the propellants, wherein a mixture of lipid crystals in combination with said therapeutically active agent is formed.

23. The method of claim 22 wherein said mixture is administered via nasal inhalation utilizing a metered dose device.

24. The method of claim 22 wherein said aerosolized mixture of lipid crystals in combination with at least one therapeutically active agent is administered via oral inhalation utilizing a metered dose device.

25. The method of claim 22 wherein the lipids are phospholipids, neutral lipids or mixtures thereof.

26. The method of claim 25 wherein the phospholipids are any of a class known as phosphatidylcholines.

27. The method of claim 26 wherein the phosphatidylcholine is any fully saturated diacyl phosphatidylcholine.

28. The method of claim 25 wherein the phospholipid is diacylphosphatidylglycerol.

29. The method of claim 25 wherein the phospholipid is diacylphosphatidylethanolamine.

30. The method of claim 25 wherein the phospholipid is diacylphosphatidylserine.

31. The method of claim 25 wherein the phospholipid is diacylphosphatidylinositol.

32. The method of claim 25 wherein the phospholipid is a sphingomyelin.

33. The method of claim 25 wherein the phospholipid is Cardiolipin.

34. The method of claim 25 wherein the phospholipid is a lysophospholipid.

35. The method of claim 25 wherein the phospholipid is plasmalogen.

36. The method of claim 25 wherein the phospholipid is a diether phosphonolipid.

37. The method of claim 25 wherein the phospholipid is a dialkylphospholipid.

38. The method of claim 22 wherein the carbohydrates are glucose, fructose, galactose, pneumogalactan or dextrose.

39. The method of claim 22 wherein the protein is selected from albumin and pulmonary surfactant specific proteins A or B or C or D or mixtures thereof.

40. The method of claim 22 wherein the cholesteryl ester is cholesteryl palmitate, cholesteryl oleate or cholesteryl stearate.

41. The method of claim 22 wherein the propellants are selected to be fluorocarbons, chlorofluorocarbons, hydrofluorocarbons, carbon dioxide, or mixtures thereof.

42. The method of claim 22 wherein said therapeutically active agent is an anti-inflammatory agent, de-congestive agent, antibiotic agent, anti-viral agent, anti-fungal agent, anti-parasitic agent, gene therapy agent, or combination thereof.

43. The method of claim 42 wherein said anti-inflammatory agent is a corticosteroid.

44. The method of claim 43 wherein the corticosteroid is betamethasone diproprionate, betamethasone valerate or combinations thereof.

45. The method of claim 42 wherein said therapeutically active agent is a de-congestive agent.

46. The method of claim 45 wherein said decongestive agent is phenylephrine HCL, phenylephrine bitartrate or combination thereof.

47. The method of claim 42 wherein said therapeutically active agent is an antibiotic.

48. The method of claim 47 wherein said antibiotic is erythromycin, amoxicillin, zythromax, clavulanic acid or combinations thereof.

49. The method of claim 42 wherein said therapeutically active agent is an anti-viral agent.

50. The method of claim 49 wherein said anti-viral agent is acyclovir.

51. The method of claim 42 wherein said therapeutically active agent is a gene therapy agent.

52. The method of claim 51 wherein said gene therapy agent comprises a nucleic acid.

53. The method of claim 22 wherein 95 percent of said lipid crystals demonstrate a particle size no greater than 4 microns in diameter.

* * * * *